United States Patent [19]

Alfano et al.

[11] Patent Number: 4,930,516

[45] Date of Patent: Jun. 5, 1990

[54] METHOD FOR DETECTING CANCEROUS TISSUE USING VISIBLE NATIVE LUMINESCENCE

[76] Inventors: Robert R. Alfano; Michele A. Alfano, both of 3777 Independence Ave., Bronx, N.Y. 10463

[21] Appl. No.: 186,747

[22] Filed: Apr. 25, 1988

Related U.S. Application Data

[63] Continuation of Ser. No. 796,859, Nov. 13, 1985, abandoned.

[51] Int. Cl.$^5$ ............................................. A61B 5/00
[52] U.S. Cl. .................................... 128/665; 128/395
[58] Field of Search ............ 128/633, 634, 665, 303.1, 128/395, 398; 356/435

[56] References Cited

U.S. PATENT DOCUMENTS

| | | | |
|---|---|---|---|
| 3,647,299 | 3/1972 | Lavallee | 128/663 |
| 3,789,832 | 2/1974 | Damadian | 128/653 |
| 4,170,987 | 10/1979 | Anselmo et al. | 128/665 |
| 4,213,462 | 7/1980 | Sato | 128/634 |
| 4,479,499 | 10/1984 | Alfano | 128/665 |
| 4,569,354 | 2/1986 | Shapiro et al. | 128/665 |
| 4,637,400 | 1/1987 | Marcus | 128/653 |
| 4,718,417 | 1/1988 | Kittrell et al. | 128/634 |

FOREIGN PATENT DOCUMENTS 2125986  3/1984  United Kingdom ..................... 128/

OTHER PUBLICATIONS

Spears et al., "Fluorescence of Experimental Atheromatous Plaques with Hemotoporphyrin Derivative", pp. 395–399, vol. 71, Feb. 1983, J. Clin. Invest.

*Primary Examiner*—Ruth S. Smith
*Attorney, Agent, or Firm*—Irving M. Kriegsman

[57] ABSTRACT

A method and apparatus for detecting the presence of cancerous tissue using visible luminescence. The tissue to be examined is excited with a beam of monochromatic light that causes the tissue to fluoresce over a spectrum of wavelengths. The intensity at which the excited tissue fluoresces can be measured either over a spectrum or at a predetermined number of preselected wavelengths. By determining the wavelength(s) at which maximum intensity(ies) are attained for the tissue in question and by comparing these peak wavelengths, either visually or electronically, to the peak wavelength(s) derived from a known non-cancerous tissue, or by comparing the spectrum of the excited tissue with the spectrum of a known noncancerous tissue one can determine the carcinomatoid status of the tissue in question. The invention is based on the discovery that the visible luminescence spectra for cancerous and non-cancerous tissue are substantially different and that the differences are such that visible luminescence from tissue can be used to detect the presence of cancer.

9 Claims, 4 Drawing Sheets

METHOD FOR DETECTING CANCEROUS TISSUE USING VISIBLE NATIVE LUMINESCENCE

This application is a continuation-in-part of application Ser. no. 796,859, filed 11-13-85, now abandoned.

BACKGROUND OF THE INVENTION

The present invention relates to a method and apparatus for detecting the presence of cancerous tissue and more particularly to a method and apparatus for detecting cancerous tissue using visible luminescence.

Because a sufficiently effective method has not yet been developed to prevent cancer, cancer research has focused on the most effective ways to cure an organism that is diagnosed as having a cancer. As different as the various forms of treatment have been—ranging from excision to radiation to chemotherapy—all treatments have relied on one crucial step, detection of the cancerous tissue. The importance of detection cannot be stressed enough. Early detection not only indicates the presence of a cancer but also may give an indication as to where the cancer originated and as to what type of treatment will be the most safe and effective method. Early detection can provide such benefits because it reveals the state of maturation of the cancer cell. Cancer cells are clonal cells of a single "founder" cell that is the result of some mutation of the normal cell for the particular tissue. As a result of the mutation, the founder cell replicates and divides, eventually forming a mass of cells called a tumor. Tumors are harmful to an organism because they prolife rate at a metabolic rate that exceeds that of the normal neighboring cells. As a result, the tumor grows at the expense of the normal neighboring tissue, ultimately destroying the normal tissue. One of the reasons why it is so difficult to completely cure an organism of cancer is that cancer cells have the ability to disseminate throughout the organism via lymphatic or circulatory systems and to create new tumors where they arrive. However, this ability to disseminate comes only to those cells that have lost the characteristic membrane glycoproteins of the mutated tissue. For this reason, it takes a while before cancer can spread. An advantage to early detection is that the cells can be examined for characteristic properties such as cell size and shape to determine the source of the cancer cells.

Clearly, the importance of an accurate technique that can be utilized in vivo or in vitro cannot be minimized. The advantage of an in vivo and in vitro technique is that sensitive tissue may be tested, relatively undisturbed, for example, with the use of an inserted optical fiber probel.

Presently, the diagnosis of cancer mainly relies on X-rays, nuclear magnetic resonance, nuclear radiation or invasive methods based on chemical laboratory analysis and biopsy. In view of the dangerous side effects of X-rays, nuclear radiation, and biopses it appears that a definite need exists for a new technique for detecting cancer which can either eliminate or reduce the necessity of X-rays, nuclear radiation, and biopsies.

Although there exist many effective methods for detecting cancer, very few methods are based exclusively on the intrinsic properties of the cell and, as a result, interfere with normal tissues. For example, Hematoporphyrin derivative (HPD), which absorbs preferentially to cancerous tissue, is currently employed as a photosensitizer of tumors for photoradiation therapy. Unfortunately HPD interferes with normal tissue and does not make a good in vivo technique for detection. Flavins and porphyrin found in abundance for their effectiveness at transferring electrons in subcellular organelles known as mitochrondria are known to fluoresce in the visible light portion of the luminescence spectra.

Optical spectroscopy and laser technology offer new techniques for detection and characterization of physical and chemical changes which occur in diseased tissue, either in vivo or in vitro. This lends itself to a new approval for diagnosis of pathological changes in tissue.

The present invention is based, at least in part, on the discovery that the fluorescence spectra profiles of cancerous tissue is different from normal tissue spectra and the discovery that the fluorescence peak is blue-shifted (shifted to lower wavelengths) in areas corresponding to flavin and porphyrin peaks and the red peaks are reduced in intensity. Because this blue-shift is an intrinsic property of the tissue, normal tissue is unaffected, making the monitoring of these fluorescence spectra an especially safe in vivo technique. A possible explanation for the blue-shift and change in fluorescence spectral profile of cancerous tissue is that the flavins and porphyrins are in different environments that effect the fluorescence of these molecules. Flavins may blue-shift when a protein closely associataed to the flavin acquires net positive charge relative to its native state. Porphyrins, which fluoresce only in cancerous tissue are probably in the dissociated state since this is the only form that fluoresces. The abundance of free prophyrins in cancerous tissue may result from a reduction of the metal ion that serves to build the porphyrins in the proteins.

Based on this knowledge that certain biological molecules fluoresce differently in cancerous and non-cancerous tissue and that spectra changes shape and shift to the blue for these molecules present both a necessary and sufficient criterion for determination of cancerous tissue, it would appear that a definite need exists for an accurate, precise, simple and safe technique for detecting this fluorescence spectral shift and shape.

In U.S. Pat. No. 2,437,916 to W. F. Greenwald there is described a technique for examining living tissue which involves illuminating the tissue with a beam of light and then measuring the intensity of the reflected light at certain wavelengths ranges using a phototube and different colored filters.

In U.S. Pat. No. 3,674,008 to C. C. Johnson there is described an instrument which quantitatively measures optical density of a transilluminated body portion. The instrument comprises a controllable, relatively low-frequency oscillator generating pulses which are applied to a light source through a first expand and delay circuit. A light-conducting source to one side of the body portion and a similar means optically couples another side of the body portion to a light detector. Alternatively, the light source and detector may be placed directly on the body portion. After compensation for ambient light, the output of the detector is coupled to a sample and hold circuit which is triggered by the controllable oscillator through a second expand and delay circuit. The stored signal in the sample and hold circuit is proportional to transmittance and calibrated display means. Methods of using the instrument in diagnosis are discussed, as are further applications to spectrophotometeric determinations.

In U.S. Pat. No. 3,963,019 to R. S. Quandt there is described a method and apparatus for detecting changes in body chemistry, for example, glycemia, in which a beam of light is projected into and through the aqueous humor of the patient's eye. An analyzer positioned to detect the beam on its exit from the patient's eye compares the effect the aqueous humor has on said beam against a norm. An excess or deficiency of glucose present in the aqueous humor produces a corresponding positive or negative variation in the exiting beam and thereby indicates a hyper or hypo glycemia condition in the body chemistry of the patent being tested.

In U.S. Pat. No. 4,029,085 to D. P. DeWitt et al there is described a method for determining the bilirubin concentration in the blood serum of a person from measurement of the spectral reflectance of the skin. The disclosed method detects the severity of jaundice, common neonatal condition, and enables determination of the type of treatment regimen needed to prevent the billirubin level from becoming sufficiently high to cause kernicterus which can result in brain damage. The method includes measuring the reflectance of the skin within a predetermined frequency spectrum, and more particularly, at a number of specific wavelengths in the visible portion of the spectrum.

In U.S. Pat. No. 4,290,433 to Robert R. Alfano there is described a method and apparatus for detecting the presence of caries a human teeth using visible luminescence. A region to be examined is excited with a beam of monochromatic light. The intensity of the visible light emitted from the region is measured at two predetermined wavelengths, one where the intensity dependence of the spectra is about the same for caries and non caries and the other where the relative intensity changes significantly in the presence of caries. A signal corresponding to the difference in the two intensities is obtained and then displayed. By first determining the magnitude of the difference signal at a nondecayed region, any increases in the magnitude as other regions are probed on the discovery that the visible luminescence spectra for decayed and nondecayed regions of a human tooth are substantially different and that the differences are such that visible luminescence from teeth can be used to detect the presence of caries.

In *Medical and Biological Engineering*, Vol 6, No 4 Aug., 1968, pp. 409-413 there is described a technique for tissue identification during needle puncture by reflection spectrophotometry.

SUMMARY OF THE INVENTION

It is an object of this invention to provide a new, rapid, and improved technique for detecting the presence of cancerous tissue.

It is another object of the invention to provide a technique for detecting the presence of cancerous tissue which does not involve the use of X-rays.

It is still another object of this invention to provide a technique for detecting the presence of cancerous tissue that does not involve the use of other potentially harmful radiation, such as ultraviolet radiation or nuclear radiation.

It is yet still another object of this invention to provide a technique for detecting the presence of cancerous tissue of a person which is reliable, rapid, inexpensive and easy to use.

It is another object of this invention to provide a technique for detecting the presence of cancerous tissue which does not require the use of X-ray sensitive plates or film.

It is still another object of this invention to provide a technique for detecting the presence of cancerous tissue which is suitable for use with conventional photographic film or eye an associated optical filters.

It is still another object of this invention to provide a technique for detecting the presence of cancerous tissue which is for use with photodetectors (eye, photodiodes, photomultipliers, video) and associated optical filters. It is yet still another object of this invention to provide a technique for detecting the presence of cancerous tissue using visible light as an exciting source and visible luminescence to probe for the cancerous tissue.

It is still another object of this invention to provide a new diagnostic tool for the pathologist to evaluate a biopsy in cancer and for a surgeon to evaluate if all cancerous tissue has been removed, using fluorescence spectroscopy.

It is still another object of this invention to provide a in-vivo spectroscopy diagnosis technique using an optical fiber (endoscopy) to determine cancer inside a body (i.e. stomach, lungs, urinary tract, intestinal tract, brain, colon, eye and throat).

It is still another object of this invention to provide a in-vitro spectroscopy diagnostic technique for a pathologist to test biopsy samples.

The present invention is based on the discovery that the shape of the visible luminescence spectra from normal and cancerous tissue are substantially different, and in particular, that for cancerous tissue there is a shift to the blue with different intensity peaks.

The method for detecting the presence of cancerous tissue according to the teachings of this invention are based on the above noted discovery involves, according to one embodiment of the invention, illuminating a region to be examined with a beam of monochromatic light, and then comparing the resulting luminescence spectrum with the luminescence spectrum for a normal tissue. The apparatus for detecting the presence of cancerous tissue according to the teachings of this invention and based on the above noted discovery, according to one embodiment of the invention includes a monochromatic light source, a spectrograph, a video camera, a digitizer, a computer and a display means for measuring the intensity of the emitted light over a plurality of wavelengths and displaying the difference in the spectra.

The apparatus for detecting the presence of cancerous tissue according to another embodiment of the invention includes a monochromatic light source, optical filters, a photodetector and a display means for measuring the emitted light at different wavelengths.

The foregoing and other objects and advantages will appear from the description to follow. In the description, reference is made to the accompanying drawing which forms a part thereof, and in which is shown by way of illustration a specific embodiment for practicing the invention. This embodiment will be described in sufficient detail to enable those skilled in the art to practice the invention, and it is to be understood that other embodiments may be utilized and that structural changes may be made without departing from the scope of the invention. The following detailed description is therefore, not to be taken in a limiting sense, and the scope of the present invention is best defined by the appended claims.

DETAILED DESCRIPTION

The present invention is directed to a method and apparatus for detecting the presence of cancerous tissue in a person using visible luminescence.

Figure 1:
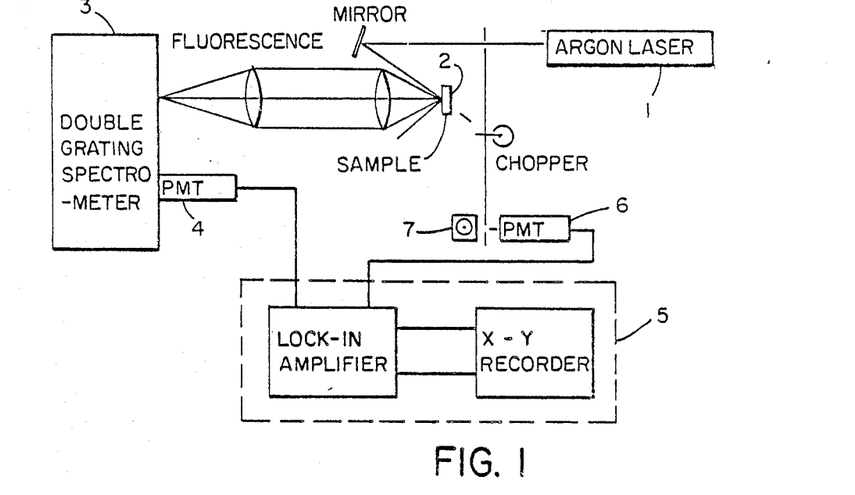
FIG. 1 is a schematic diagram of an experimental setup used to measure luminescence spectra from various tissues.

An experimental arrangement used to measure the luminescence spectra from the various tisues is shown in FIG. 1. A 10 mw Argon ion laser 1 operating a 488 nm was focused on the front surface of the tissue 2 to a spot size of about 100 um. The luminescence from the front surface was collected into a double Spe-½ m grating scanning spectrometer 3 blazed at 500 nm. A photomultiplier tube (PMT) RCA 7265 (S-20) 4 located at the exit slit of the spectrometer 3 measured the intensity at different wavelengths. The spectral bandwidth was 1.8 nm. The output of the PMT was connected to a Princeton Applied Research lock-in recorder combination 5 to display the spectrum. Both the laser output abn reference signal insert from light 7 and detected by PMT 6 were chopped at 200 Hz. The spectra were not corrected for the spectrum response of the system. Each sample emission spectrum was run three times for reproducibility. The measured spectra were stable in time and different regions yielded similar spectra.

The luminescence emitted from cancerous and normal tissues from rat prostate and kidney were investigated. The spectra from a rat female bladder tumor and a mouse bladder tumor were also measured. All tumors were subcutaneously implanted. Rat prostate tumors (R 3327 C.P,) were implanted in Fischer/Copenhagen male ($f_1$) rats and were five weeks old at the time of the testing. Rat kidney tumors were implanted in Wistor-/Lewis rats and were four weeks old. Rat Bladder tumor (TCT-4909) was implanted in a female Fischer rat and was four weeks old at the time of testing. Mouse bladder tumor (MBT-2) was implanted in a female C3HHe mouse and was also four weeks old. All tissue samples were nonnectrotic, clean free and approximately 1 gm in weight. All tissue samples were solid chunks but not cut to any particular specificity, and were few millimeters thick. Each tissue sample was placed in a clean pyrex test tube for these luminescence studies.

Figure 2A:
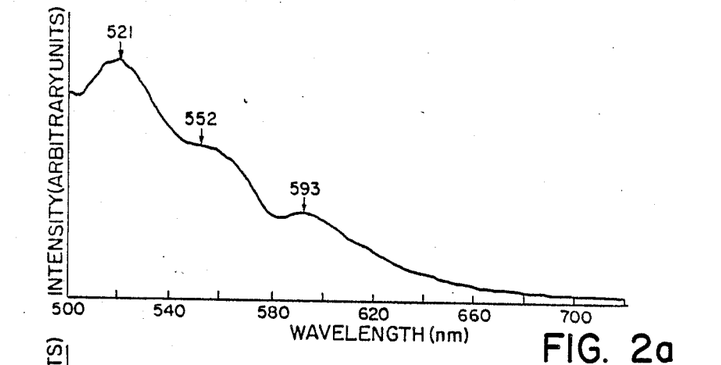
FIGS. 2(a) and 2(b) are fluorescence spectrum of rat prostate tumor and normal rat prostrate, respectively.
Figure 2B:
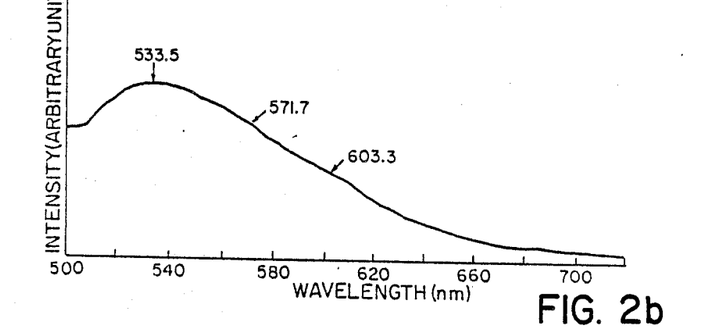
Figure 3A:
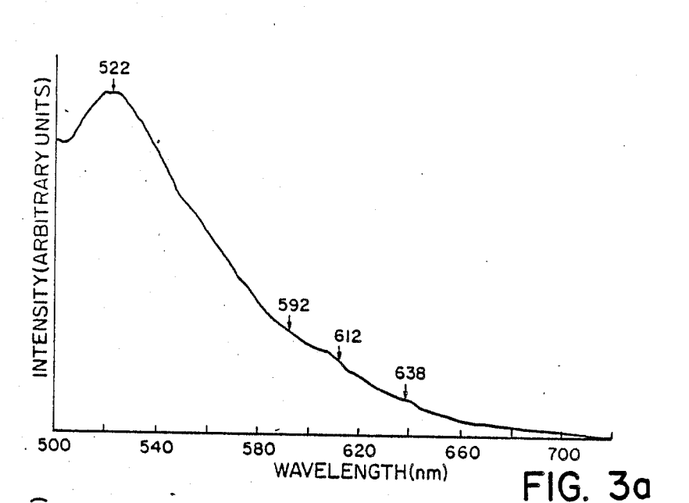
FIGS. 3(a) and 3(b) are fluorescence spectrum of rat kidney tumor and normal rat kidney, respectively.
Figure 3B:
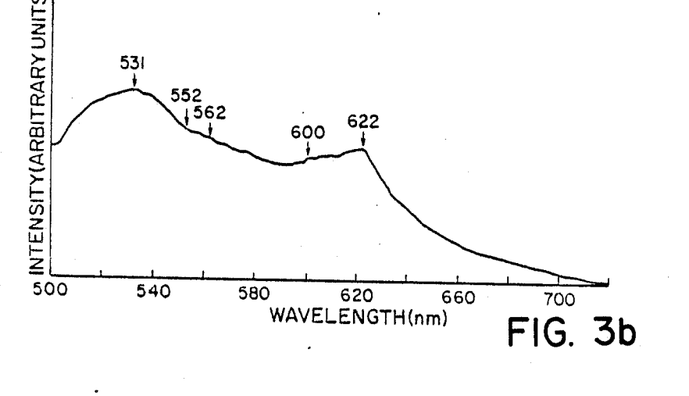
Figure 4A:
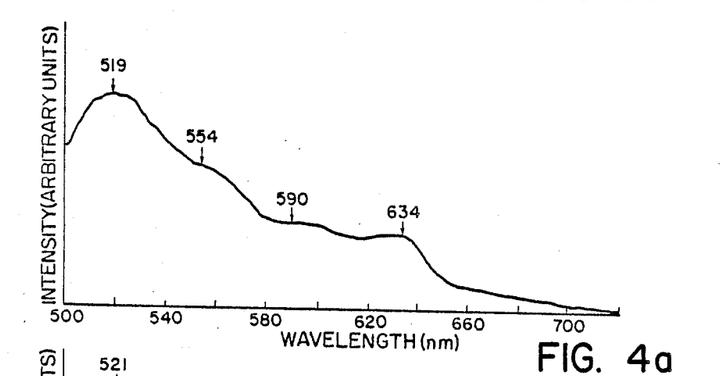
FIGS. 4(a) and 4(b) are fluorescence spectrum of rat bladder tumor and mouse bladder tumor.
Figure 4B:
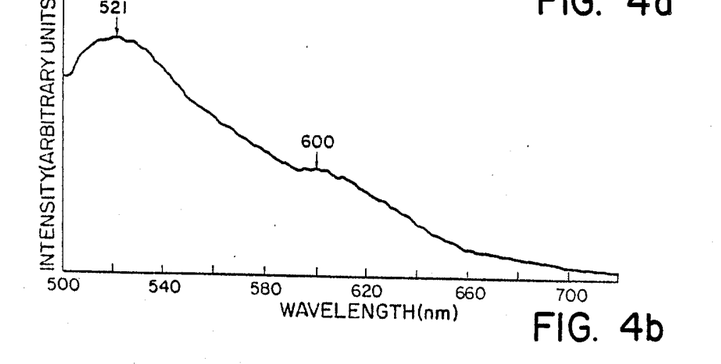

The spectral curves for the cancerous and normal tissues are displayed in FIGS. 2-4. One notices the differences in the spectra between the normal and cancerous tissues. The prominent maxima in the spectra from rat prostate tumor [FIG. 2(a)] and rat normal prostate [FIG. 2(b)] are located at 521 and 533.5 nm., respectively. The prostate tumor spectrum has two subsidiary maxims located at 552 and 593 nm while no additional maxima are recorded in the normal prostrate spectrum. In the prostate tumor spectrum there are four points of inflections located at 538.3, 571.7, 587.0, and 619.5 nm. On the decreasing side of the normal prostate curve there are two points of inflection located at 571.7 and 603.3 nm, as shown in FIG. 2(b).

The main maxima in the spectra from male rat kidney tumor [FIG. 3(a)] and normal male rat kidney [FIG. 3(b)] are also located at 522.0 and 530.6 nm., respectively. After the first prominent peak, the spectrum from the rat kidney tumor decreases monotonically and there are three small peaks located at 592, 612, and 638 nm. Along this declining side of the curve there are four inflectionary points located at 548.7, 559.3, 581.3, and 604.2 nm. However, after the first prominent peak for the normal male kidney, the spectrum declines monotonically until it reaches a wavelength at 590.8 nm where it starts to increase. Along the declined portion of the curve there are three smaller peaks located at 562, 600 and 622 nm. The spectrum also contains three inflectionary points located at 522 and 595 nm.

The salient features of the rat bladder tumor spectrum are its four peaks. [FIG. 4(a)]. The first prominent peak is located at 519.1 nm; other smaller peaks are located at 554, 590, and 634 nm. The spectrum also contains two inflectionary points locate at 567.0 and 605.2 nm. After the minimum at 614.7 nm the curve starts rising to the last peak at 634.0 nm, after which there is a fall off to zero intensity.

The salient features of the mouses bladder tumor spectrum are its two wide peaks [see FIG. 4(b)]. The first prominent peak is located at 521.0 nm, and the other at 600.0 nm. The spectrum starts declining from 610 to 648 nm after which its slope changes and decays slowly to zero. There are two points of inflection in the spectrum, one located at 559.2 nm and the other at 648.2 nm.

The summary of the results from the fluorescence measurements shows the following salient features that are found in common among the tumor spectra:

1. Locations of the prominent maxima of the tumor spectra all occur at about 521.0 nm.
2. The width of the prominent maxima are virtually the same, approximately spanning 1.5 nm.
3. Secondary peaks which are in common to all tumors occur between 590-640 nm.
4. The secondary peak which is also in common with the prostate tumor and the rat bladder tumor is in the range of 552-554 nm.
5. The secondary peak which is also in common with the rat kidney tumor and the rat bladder tumor fall in the range of 634-638 nm.

Upon analysis of the data between the two normal spectra, one recognizes the prominent maxima are located at 530-533 nm and the width of the prominent maxima are broad, each spanning 38 nm.

The most salient differences between the cancerous and the normal tissues are that the spectral profiles are very different and that the cancerous prominent maxima are blue shifted and located around 521 nm, whereas the prominent maxima of the normal tissues spectra are located at about 531 nm.

As can be seen, when protein containing fluorphors either gain positive charge ions or lose negative charge ions the fluorescence from the fluorphors have been noted to be blue shifted. The prominent maxima of all cancerous spectra exhibit in our results a 10 nm blue shift, suggesting an accumulation of positive ions, or a depletion of negative ions in the mitochrondria of cancerous cells, thus causing the flavins to emit at 521 nm instead of 531 nm.

The emission from 590–640 nm is attributed to porphyrins. In cancerous tissue the relative intensity of porphyrins bands are different, usually smaller in intensity from its normal counterpart.

Figures 5, 6:
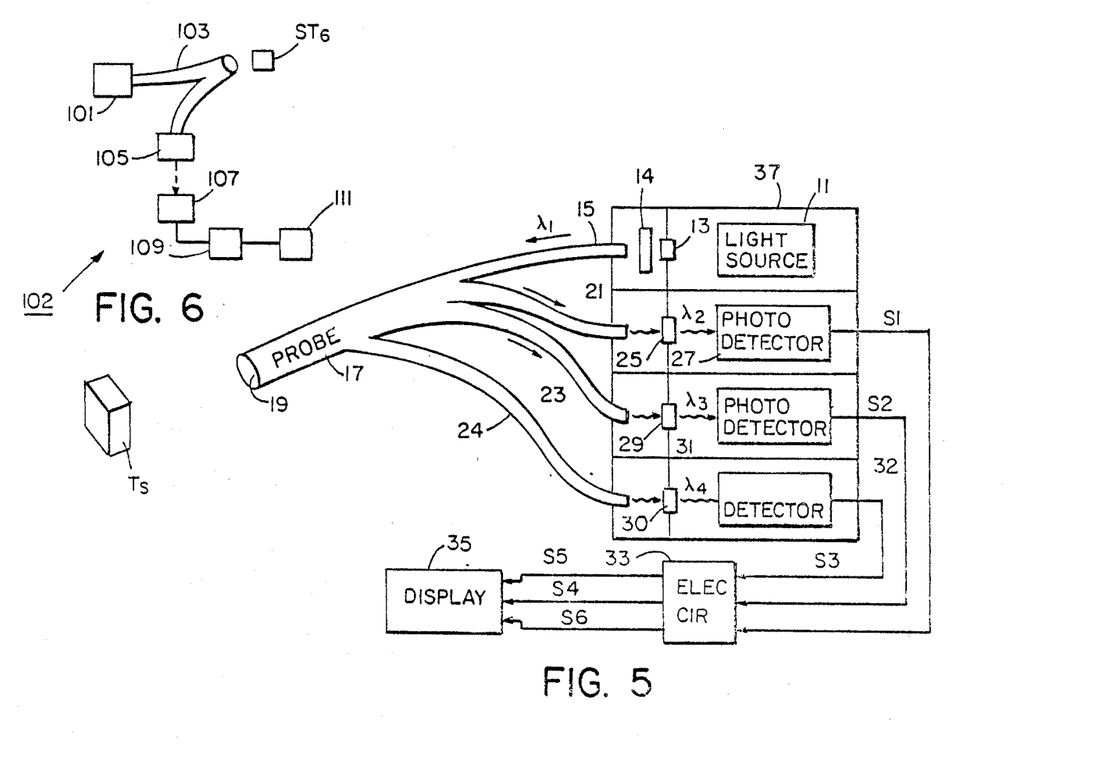
FIG. 5 is a simplified diagram of one embodiment of an apparatus of the invention.
FIG. 6 is a simplified diagram of another embodiment of the invention.

Referring now to FIG. 5 there is illustrated an embodiment of an apparatus for detecting cancerous tissue according to the teachings of this invention.

The apparatus includes a source 11 of white light, such as a tungsten-halogen filament lamp, and a narrow band filter 13. Alternatively, source 11 may comprise a laser. Light source 11 has power coupled to it from a conventional power supply (not shown). Narrow band filter 13 has a bandwidth of less than about 30 nm and preferably less than about 10 nm and is designed to pass light at a wavelength $\lambda_1$.

Light from source 11 that is passed by filter 13 is passed through a chopper 14 which removes any ambient light present and is then fed into an input leg 15 of a fiber optic probe 17. The light entering fiber optic probe 17 emerges at the probing end 19 and impinges on tissue Ts to be tested. Light from tissue Ts enters probing end 19 and is conducted out of fiber optic probe 17 through output legs 21, 23, and 24, which are located at the same end as input leg. 15.

Fiber optic probe 17 is made up basically of a bundle of optical fibers. The diameter of the bundle is preferably about ½ to 5 nm. The fibers within the bundle are preferably randomly arranged to reduce any geometrical collection effects. Fiber optic probe 17 may include a lens or lens system (not shown) at the probing end 19 so that non-contact probing may be achieved.

Light emerging from output leg 21 is passed through a narrow band filter 25 having a bandwidth of less than about 10 nm, and designed to pass light at a wavelength $\lambda_2$, and impinges on a photodetector 27. Light emerging from output leg 23 is passed through a narrow band filter 29 having a bandwidth of less than about 10 nm and designed to pass light at a wavelength $\lambda_3$, and impinges on photodetector 31. Light emerging from output leg 24 is passed through narrow band filter 30 having a bandwidth of less than 10 nm and designed to pass light of wave-length $\lambda_4$ and impinges on photodetector 32.

The value of $\lambda_1$ is between 350 and 500 nanometers. Photodetectors 27, 31 and 32 are conventional photodetectors having maximum sensitivity in the regions of interest, namely at wavelengths $\lambda_2$ and $\lambda_3$ and $\lambda_4$ respectively of the fluorescence spectra.

Figure 7:
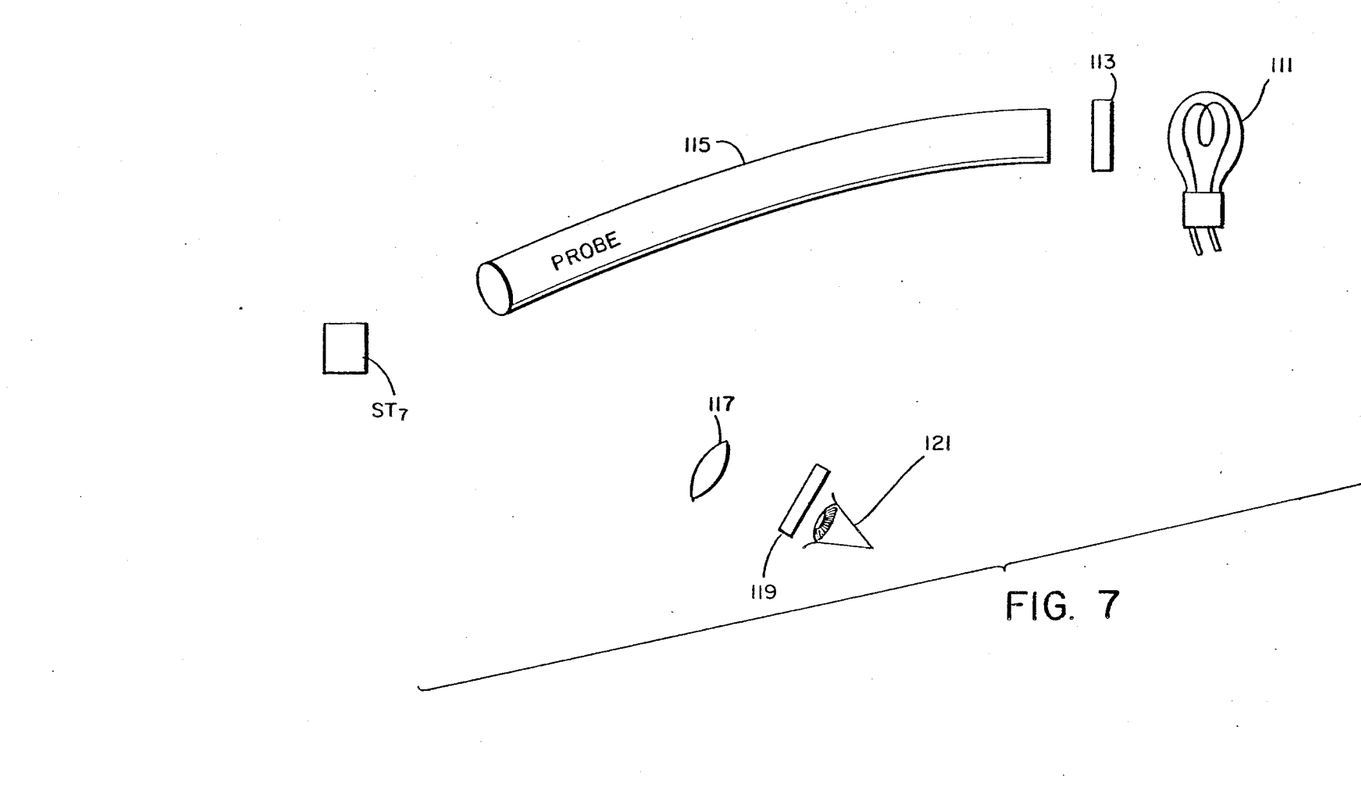
FIG. 7 is a simplified diagram of another embodiment of an apparatus of the invention.

The wavelengths are chosen where the largest difference in intensity occurs for cancerous and normal tissues i.e. $\lambda_2=531$ nm $\lambda_3=522$ nm, $\lambda_4=633$ nm. By using more detectors at more wavelengths one can more accurately determine difference in the spectra. Comparing the entire spectra using video spectroscopy, such as shown in FIG. 7, results in a more accurate way to find cancer.

Photodetectors 27, 31 and 32 each produce an electrical signal output whose magnitude S1, S2 and S3 respectively, is proportional to the intensity of the incident light. The electrical output signals from photodetectors 27, 31 and 32 are each fed into an electronic circuit 33 which produces three output signals S4, S5 and S6, one corresponding to the ratio of S1 and S3 another corresponding to the ratio of S1 and S2 and the third corresponding to the ratio of S2 to S3. The three output signals are fed into a display 35 such as a buzzer or a light or a meter or a monitor where they are displayed. The difference in the signals (i.e. the difference between signals S1 and S2 or S2 and S3) could also be used and compared.

Light source 11, narrow band filters 13, 25, 29 and 30 and photodetectors 27, 31 and 32 are preferably all situated in a light-tight compartmented housing 37.

In detecting the presence of cancerous tissue in accordance with the invention, the ratios of the three probe signals S1, S2 and S3 are first determined for a known noncancerous region for the particular organ containing the tissue under test. Any changes in the ratios between signals S1 and S2 and S3 will indicate that the tissue is cancerous.

Instead of taking the ratios between signals S1 and S2 and S3, the differences or ratios of any two as opposed to three signals, such as S1 and S2 may be used to determine the relative change of the spectra. This may be achieved using any conventional type of difference circuit for differences or a divider circuit for ratios.

Referring now to FIG. 6, there is illustrated a simplified diagram of another embodiment of the invention. Monochromatic light from a source 101 is transmitted by a fiber optic probe 103 for a sample tissue ST6 to be tested. Light from the sample tissue ST6 is transmitted by fiber optic probe 103 to a spectrograph 105 constructed so as to detect emitted light from the sample tissue ST6. The output of the spectrograph 105 is imaged by a video camera 107 whose output is fed through a digitizer 109 into a computer 111. The spectrum of emitted light along with a spectrum of emitted light for a normal tissue (for the particular organ in question) are both displayed on a display (such as a TV monitor). The difference in spectra is obtained by a computer and then displayed to determine where cancer is located.

In FIG. 7 there is shown another embodiment of the invention. Light from a source 111 is passed through a narrow band filter 113 where it is transmitted by a fiber optic probe 115 to the tissue ST7 to be tested. Light from tissue ST7 is imaged by a lens 117 through a filter wheel 119 having two or more filters where it is imaged on the eye 121. Instead of a filter wheel and eye, the light from lens 117 may be imaged onto the slit of a spectrograph and then processed as in the FIG. 6 embodiment.

What is claimed is:

1. A method for determining if tissue is cancerous comprising:
   a. exciting a tissue to be examined with a beam of light, and
   b. comparing the visible native luminescence emitted from the tissue with the visible native luminescence emitted from tissue whose condition is known.

2. A method for determining if tissue is cancerous comprising:
   a. exciting a tissue to be examined with a beam of light.
   b. observing the visible native luminescence emitted from the tissue at least two wavelengths, and
   c. determining if the tissue is cancerous in accordance with said measurements.

3. A method for detecting cancerous tissue comprising:
   a. exciting a tissue to be examined with a beam of light that is substantially monochromatic, and then b. comparing the resulting native luminescence spectrum with the native luminescence spectra for native normal and cancerous tissue.

4. A method for detecting cancerous tissue comprising:
   a. exciting a tissue to be examined with a beam of light that is at least substantially monochromatic.
   b. measuring the intensity of the visible native luminescence emitted from the tissue at least two wavelengths, and
   c. determining if the tissue is cancerous in accordance with said measurements.

5. The method of claim 4 and wherein determining if cancerous tissue is present comprises determining the ratios in intensities at at least two wavelengths and then comparing the ratios with the ratios of intensities at the same wavelengths for normal tissue.

6. The method of claim 4 and wherein determining if cancerous tissue is present includes producing a signal corresponding to the ratio between the intensities at least two wavelengths and then displaying said signals.

7. The method of claim 4 and wherein determining if cancerous tissue is present comprises producing a signal corresponding to the difference in the intensity at at least two wavelengths.

8. The method of claim 4 and wherein determining if cancerous tissue is present comprises producing a signal corresponding to the difference in spectral profiles.

9. A method for detecting cancerous tissue comprising:
   a. exciting a tissue to be examined with a beam of monochromatic light.
   b. generating a luminescence spectrum native of light emitted by the tissue, and
   c. comparing the luminescent spectrum with a luminescent spectrum for a known normal tissue.

* * * * *

REEXAMINATION CERTIFICATE (3585th)
United States Patent [19]

Alfano et al.

[11] B1 4,930,516
[45] Certificate Issued Aug. 4, 1998

[54] METHOD FOR DETECTING CANCEROUS TISSUE USING VISIBLE NATIVE LUMINESCENCE

[75] Inventors: Robert R. Alfano; Michele A. Alfano, both of Bronx, N.Y.

[73] Assignee: Laser Diagnostic Instruments Inc., Bridgewater, N.J.

Reexamination Request:
No. 90/004,585, Mar. 20, 1997

Reexamination Certificate for:
Patent No.: 4,930,516
Issued: Jun. 5, 1990
Appl. No.: 186,747
Filed: Apr. 25, 1988

Related U.S. Application Data

[63] Continuation of Ser. No. 796,859, Nov. 13, 1985, abandoned.

[51] Int. Cl.$^6$ ............................................. A61B 5/00
[52] U.S. Cl. .................. 600/477; 600/478; 607/901
[58] Field of Search ........................... 600/476–478

[56] References Cited

U.S. PATENT DOCUMENTS

| | | | |
|---|---|---|---|
| Re. 31,815 | 1/1985 | Alfano | 128/665 |
| 3,494,354 | 2/1970 | Yokota et al. | |
| 4,070,113 | 1/1978 | Frazer et al. | 356/39 |
| 4,071,020 | 1/1978 | Pugliese | 356/317 |
| 4,207,892 | 6/1980 | Binder | 600/476 |
| 4,449,535 | 5/1984 | Renault | |
| 4,534,360 | 8/1985 | Williams | 600/473 |
| 4,556,057 | 12/1985 | Hiruma et al. | 600/476 |
| 4,577,110 | 3/1986 | MacBride et al. | |
| 4,641,650 | 2/1987 | Mok | 606/12 |
| 4,649,275 | 3/1987 | Nelson et al. | 600/425 |
| 4,675,300 | 6/1987 | Zare et al. | |
| 4,675,529 | 6/1987 | Kushida | 606/15 |
| 4,751,188 | 6/1988 | Valet | 436/63 |
| 4,784,135 | 11/1988 | Blum et al. | 606/3 |
| 4,817,623 | 4/1989 | Stoddart et al. | |
| 4,913,142 | 4/1990 | Kittrell et al. | 606/7 |

FOREIGN PATENT DOCUMENTS

Sho58-118948   7/1983   Japan.

OTHER PUBLICATIONS

Galeotti et al., "On the Fluorescence of NAD(P)H in Whole-Cell Preparations of Tumours and Normal Tissues," Eur. J. Biochem., 17:485–96 (1970).

*Primary Examiner*—Ruth S. Smith

[57] ABSTRACT

A method and apparatus for detecting the presence of cancerous tissue using visible luminescence. The tissue to be examined is excited with a beam of monochromatic light that causes the tissue to fluoresce over a spectrum of wavelengths. The intensity at which the excited tissue fluoresces can be measured either over a spectrum or at a predetermined number of preselected wavelengths. By determining the wavelength(s) at which maximum intensity (ies) are attained for the tissue in question and by comparing these peak wavelengths, either visually or electronically, to the peak wavelength(s) derived from a known non-cancerous tissue, or by comparing the spectrum of the excited tissue with the spectrum of a known noncancerous tissue one can determine the carcinomatoid status of the tissue in question. The invention is based on the discovery that the visible luminescence spectra for cancerous and non-cancerous tissue are substantially different and that the differences are such that visible luminescence from tissue can be used to detect the presence of cancer.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 5-8 are cancelled.

Claims 1-4 and 9 are determined to be patentable as amended.

New claims 10-63 are added and determined to be patentable.

1. A method for determining if tissue is cancerous comprising:
   a. exciting a tissue to be examined with a beam of light, *said beam of light having a wavelength appropriate to cause visible native luminescence in the tissue at around 521 nm,* and
   b. comparing the visible native luminescence *at around 521 nm* emitted from the tissue with the visible native luminescence *at around 521 nm* emitted from tissue whose condition is known.

2. A method for determining if tissue is cancerous comprising:
   a. exciting a tissue to be examined with a beam of light, *said beam of light being at least substantially monochromatic and having a wavelength between 350 nm and 500 nm.*
   b. observing the visible native luminescence emitted from the tissue at [least two wavelengths] *a first emission wavelength of around 521 nm and at a second emission wavelength between 590-640 nm,* and
   c. determining if the tissue is cancerous in accordance with said measurements.

3. A method for detecting cancerous tissue comprising:
   a. exciting a tissue to be examined with a beam of light that is *at least* substantially monochromatic, [and then] *said beam of light having a wavelength between 350 nm and 500 nm,*
   b. *generating a native luminescence spectrum of light emitted by the tissue, said native luminescence spectrum including luminescence at around 521 nm, and*
   c. comparing the resulting native luminescence spectrum with the native luminescence spectra for [native] normal and cancerous tissue.

4. A method for detecting cancerous tissue comprising:
   a. exciting a tissue to be examined with a beam of light that is at least substantially monochromatic, *said beam of light having a wavelength between 350 nm and 500 nm,*
   b. measuring the intensity of the visible native luminescence emitted from the tissue at *at* least two wavelengths *selected from the group consisting of around 521 nm, about 531 nm and between 590-640 nm,* and
   c. determining if the tissue is cancerous in accordance with said measurements.

9. A method for detecting cancerous tissue comprising:
   a. exciting a tissue to be examined with a beam of *at least substantially* monochromatic light, *said beam of at least substantially monochromatic light having a wavelength between 350 nm and 500 nm,*
   b. generating a luminescence spectrum native of light emitted by the tissue, *said luminescence spectrum including luminescence at about 531 nm,* and
   c. comparing the luminescent spectrum with a *corresponding* luminescent spectrum for a known normal tissue.

*10. The method as claimed in claim 1 wherein said beam of light is at least substantially monochromatic.*

*11. The method as claimed in claim 10 wherein said beam of light has a wavelength between 350 nm and 500 nm.*

*12. The method as claimed in claim 11 wherein said beam of light is laser light.*

*13. The method as claimed in claim 12 wherein said beam of light has a wavelength of 488 nm.*

*14. The method as claimed in claim 1 wherein said beam of light is produced by a white light lamp.*

*15. The method as claimed in claim 1 wherein said beam of light is at least substantially monochromatic and is produced by the combination of a white light lamp and a narrow band filter, said narrow band filter being designed to pass light within a narrow wavelength band between 350 nm and 500 nm.*

*16. The method as claimed in claim 1 wherein said exciting step comprises exciting the tissue in vivo with said beam of light.*

*17. The method as claimed in claim 1 wherein said exciting step comprises transmitting said beam of light to the tissue using an endoscope.*

*18. The method as claimed in claim 1 wherein the tissue to be examined is selected from the group consisting of stomach, lung, urinary tract, intestinal tract, brain, colon, eye and throat tissues.*

*19. The method as claimed in claim 1 wherein the tissue to be examined is one of a cancerous tissue and a normal tissue.*

*20. The method as claimed in claim 2 wherein said first emission wavelength is 522 nm and wherein said second emission wavelength is 633 nm.*

*21. The method as claimed in claim 2 wherein said determining step comprises determining a ratio of intensities at said first and second emission wavelengths for the tissue being examined and then comparing said ratio to standards obtained from known normal and cancerous tissues.*

*22. The method as claimed in claim 2 wherein said determining step comprises determining a difference of intensities at said first and second emission wavelengths for the tissue being examined and then comparing said difference to standards obtained from known normal and cancerous tissues.*

*23. The method as claimed in claim 2 wherein said exciting step comprises exciting the tissue in vivo with said beam of light.*

*24. The method as claimed in claim 2 wherein said exciting step comprises transmitting said beam of light to the tissue using an endoscope.*

*25. The method as claimed in claim 2 wherein the tissue to be examined is selected from the group consisting of stomach, lung, urinary tract, intestinal tract, brain, colon, eye and throat tissues.*

*26. The method as claimed in claim 2 wherein the tissue to be examined is one of a cancerous tissue and a normal tissue.*

27. The method as claimed in claim 2 wherein said beam of light is produced by the combination of a white light lamp and a narrow band filter, said narrow band filter being designed to pass light within a narrow wavelength band between 350 nm and 500 nm.

28. The method as claimed in claim 3 wherein the tissue to be examined is one of a cancerous tissue and a normal tissue.

29. The method as claimed in claim 3 wherein said luminescence spectrum also includes luminescence at 552–554 nm.

30. The method as claimed in claim 29 wherein said luminescence spectrum further includes luminescence at 590–640 nm.

31. The method as claimed in claim 4 wherein the tissue to be examined is one of a cancerous tissue and a normal tissue.

32. The method as claimed in claim 4 wherein said determining step comprises determining a ratio of intensities at said at least two emission wavelengths for the tissue being examined and then comparing said ratio to standards obtained from known cancerous and normal tissues.

33. The method as claimed in claim 32 wherein said ratios are calculated for wavelengths where the largest difference in intensity occurs for cancerous and normal tissues.

34. The method as claimed in claim 4 wherein said determining step comprises determining a difference of intensities at said at least two emission wavelengths for the tissue being examined and then comparing said difference to standards obtained from known cancerous and normal tissues.

35. The method as claimed in claim 4 wherein said exciting step comprises exciting the tissue in vivo with said beam of light.

36. The method as claimed in claim 4 wherein said exciting step comprises transmitting said beam of light to the tissue using an endoscope.

37. The method as claimed in claim 4 wherein the tissue to be examined is selected from the group consisting of stomach, lung, urinary tract, intestinal tract, brain, colon, eye and throat tissues.

38. The method as claimed in claim 4 wherein said measuring step comprises measuring the visible native luminescence emitted from the tissue at about 531 nm and at 590–640 nm.

39. The method as claimed in claim 38 wherein said measuring step comprises measuring the visible native luminescence emitted from the tissue at 531 nm and at 633 nm.

40. The method as claimed in claim 4 wherein said measuring step comprises using a pair of narrow band filters to select light at said two wavelengths and then detecting the selected light.

41. The method as claimed in claim 9 wherein said beam of light is substantially monochromatic and has a wavelength in the range of 350 nm to 500 nm.

42. The method as claimed in claim 9 wherein the tissue to be examined is one of a cancerous tissue and a normal tissue.

43. A method for detecting cancerous tissue comprising:
  a. exciting a tissue to be examined with a beam of light that is at least substantially monochromatic, said beam of light having a wavelength between 350 nm and 500 nm,
  b. measuring the intensity of the visible native luminescence emitted from the tissue at around 521 nm and at about 531 nm, and
  c. determining if the tissue is cancerous in accordance with said measurements.

44. A method for detecting cancerous tissue comprising:
  a. exciting a tissue to be examined with a beam of light that is at least substantially monochromatic, said beam of light having a wavelength between 350 nm and 500 nm,
  b. measuring the intensity of the visible native luminescence emitted from the tissue at at least two emission wavelengths selected from the group consisting of 522 nm, 531 nm and 633 nm, and
  c. determining if the tissue is cancerous in accordance with said measurements.

45. The method as claimed in claim 44 wherein said determining step comprises calculating a ratio of intensities at two of said emission wavelengths of the group consisting of 522 nm, 531 nm and 633 nm for the tissue being examined and comparing said ratio to standards from tissues whose conditions are known.

46. The method as claimed in claim 44 wherein said determining step comprises calculating a difference of intensities at two of said emission wavelengths of the group consisting of 522 nm, 531 nm and 633 nm for the tissue being examined and comparing said difference to standards from tissues whose conditions are known.

47. The method as claimed in claim 44 wherein said measuring step comprises measuring the intensity of the visible native luminescence emitted from the tissue using a spectrograph and a video camera.

48. A method for determining the carcinomatoid status of a cancerous or normal tissue, the cancerous or normal tissue being selected from the group consisting of cancerous or normal prostate tissue and cancerous or normal bladder tissue, said method comprising:
  a. exciting the cancerous or normal tissue to be examined with a beam of light having a wavelength appropriate to cause visible native luminescence in the range of 552–554 nm in the cancerous or normal tissue being examined, and
  b. comparing the visible native luminescence in the range of 552–554 nm emitted from the cancerous or normal tissue being examined with the visible native luminescence in the range of 552–554 nm emitted from cancerous or normal tissue whose carcinomatoid condition is known.

49. A method for detecting cancerous tissue comprising:
  a. exciting a tissue to be examined with a beam of light, said beam of light having a wavelength appropriate to cause visible native luminescence in the tissue at around 521 nm,
  b. generating a native luminescence spectrum of light emitted by the tissue, said luminescence spectrum including luminescence at around 521 nm, and
  c. comparing the resulting native luminescence spectrum with the native luminescence spectra for tissue whose condition is known.

50. The method as claimed in claim 49 wherein said beam of light has a wavelength of 350 nm.

51. The method as claimed in claim 49 wherein said luminescence spectrum also includes luminescence at 590–640 nm.

52. A method for determining if tissue is cancerous comprising:
  a. exciting a tissue to be examined with a beam of light, said beam of light being at least substantially monochromatic and having a wavelength between 350 nm and 500 nm,
  b. observing the visible native luminescence emitted from the tissue at at least two emission wavelengths selected from the group consisting of around 521 nm, about 531 nm, 552–554 nm and 590–640 nm, and c. determining if the tissue is cancerous on the basis of said observations.

53. The method as claimed in claim 52 wherein said beam of light is produced by the combination of a white light lamp and a narrow band filter.

54. A method for determining if tissue is cancerous comprising:

a. exciting a tissue to be examined with a beam of at least substantially monochromatic light, said beam of at least substantially monochromatic light having a wavelength between 350 nm and 500 nm, b. generating a native luminescence spectrum of light emitted by the tissue, said luminescence spectrum extending from 500 nm to 720 nm, and c. comparing the native luminescent spectrum from the tissue with corresponding native luminescent spectra from standard tissues.

55. The method as claimed in claim 54 wherein said beam of at least substantially monochromatic light has a wavelength of 488 nm.

56. The method as claimed in claim 54 wherein the tissue is located inside a body and wherein said exciting step comprises transmitting said beam of light to the tissue using an endoscope.

57. The method as claimed in claim 54 wherein said exciting step comprises transmitting said beam of light to the tissue using a fiber optic probe.

58. A method for determining if tissue is cancerous comprising:

a. exciting the tissue to be examined with a beam of at least substantially monochromatic light, said beam of at least substantially monochromatic light having a wavelength between 350 nm and 500 nm;

b. observing the visible native luminescence emitted from the tissue at at least a first emission wavelength, said first emission wavelength being selected from the group consisting of around 521 nm, about 531 nm and 552–554 nm; and c. determining if the tissue is cancerous on the basis of said observations.

59. The method as claimed in claim 58 wherein said first emission wavelength is selected from the group consisting of around 521 nm and about 531 nm.

60. The method as claimed in claim 59 wherein said observing step further comprises observing the visible native luminescence emitted from the tissue at a second emission wavelength, said second emission wavelength being 590–640 nm.

61. The method as claimed in claim 60 wherein said observing step is performed using an eye.

62. The method as claimed in claim 60 wherein the tissue being examined is one of a cancerous tissue and a normal tissue.

63. The method as claimed in claim 60 wherein said second emission wavelength is 633 nm.

\* \* \* \* \*